United States Patent
Persuitti et al.

(10) Patent No.: US 7,016,734 B2
(45) Date of Patent: Mar. 21, 2006

(54) 360-DEGREE FLAT-SURFACE MECHANICAL STOP FOR LEAD CONNECTOR BLOCK AND SETSCREW SYSTEM

(75) Inventors: Kevin J. Persuitti, Andover, MN (US); Timothy P. Linger, Wadsworth, OH (US); Toua Vang, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 512 days.

(21) Appl. No.: 10/430,847

(22) Filed: May 6, 2003

(65) Prior Publication Data
US 2004/0225334 A1 Nov. 11, 2004

(51) Int. Cl.
*A61N 1/375* (2006.01)

(52) U.S. Cl. .......................... 607/37; 607/36; 411/393; 439/814; 403/362

(58) Field of Classification Search .................. 607/36, 607/37; 403/362; 292/350; 439/810, 814; 411/393
See application file for complete search history.

(56) References Cited

U.S. PATENT DOCUMENTS 4,764,132 A * 8/1988 Stutz, Jr. .................... 607/116
5,669,790 A * 9/1997 Carson et al. ............... 439/668
5,989,077 A * 11/1999 Mast et al. .................. 439/814
6,112,120 A * 8/2000 Correas ........................ 607/37

* cited by examiner

Primary Examiner—Mark Bockelman
Assistant Examiner—Eric Bertram
(74) Attorney, Agent, or Firm—Nikolai & Mersereau, P.A.; Thomas J. Nikolai

(57) ABSTRACT

A connector block and associated locking setscrew for an implantable electronic tissue stimulating device are designed to eliminate thread damage to the setscrew which is a cause of the setscrew becoming stuck in the connector block. The threaded bore in the connector that is adapted to receive the setscrew is provided with an undercut at the end of the threaded bore where the undercut provides an annular, 360-degree flat surface that is normal to the longitudinal axis of the setscrew receiving bore. The setscrew employed is designed to have a shoulder machined a predetermined distance below the terminus of the final thread by machining a reduced diameter portion on the distal end of the setscrew. Now, when the setscrew is inserted into its threaded bore, the shoulder on the setscrew and the flat surface on the undercut in the connector block meet, preventing any portion of the screw threads from extending beyond the internal threads formed in the setscrew receiving bore of the connector block.

5 Claims, 5 Drawing Sheets

360-DEGREE FLAT-SURFACE MECHANICAL STOP FOR LEAD CONNECTOR BLOCK AND SETSCREW SYSTEM

BACKGROUND OF THE INVENTION

I. Field of the Invention

This invention relates to connectors for coupling a lead for a tissue stimulating devices, such as a cardiac pacemaker or pacemaker defibrillator, to a pulse generator, and more particularly to a mechanical connector that eliminates the potential for the setscrew becoming locked or stuck in the connector block due to thread damage.

II. Discussion of the Prior Art

Implantable medical tissue stimulators including pacemakers, defibrillators and neural stimulators are used to stimulate tissue such as cardiac tissue or spinal cord tissue with electrical signal. Such tissue stimulators are now quite common and typically comprise a hermetically sealed housing or can containing an electronic circuit and power supply for producing electrical impulses under control of a programmed microprocessor. The pulse generator is connected to target tissue by means of a suitable medical lead. Such leads typically comprise an elongated flexible lead body having a proximal end and a distal end. Disposed at the distal end of the lead are one or more tissue contacting electrodes. The electrodes are connected by wires running through the lead body to associated contacts on a terminal pin at the proximal end of the lead.

The proximal lead terminal pin is adapted to be inserted into a longitudinal bore formed in a header of the stimulating pulse generator. Contained within the header are one or more conductive connector blocks that are connected to feedthrough pins that pass through hermetic seals to join with input and/or output nodes of the electronic circuit contained within the housing. The connector blocks will typically have apertures formed therethrough in alignment with the bore of the header, allowing the proximal lead terminal pin to be inserted through them. To lock the lead in place, the connector blocks will typically include a threaded bore that extends transverse to the longitudinal direction of the bore in the header. Setscrews are inserted into these threaded bores and tightened down against contact areas on the proximal lead terminal. In prior art connector block designs, the last thread convolution or groove gradually reduces in size and terminates within 360 degrees around the circumference. As such, when a setscrew is screwed all the way down when no lead terminal is present in the longitudinal bore of the connector block, the leading thread of the setscrew can extend past the existing threaded area of the connector block. This causes the unmated portion of the leading thread of the setscrew to scrape against a non-threaded area of the connector block. When torque is applied in this situation, the sharp edge on the leading thread of the setscrew will often break off, creating a burr. Furthermore, given the short length of the setscrews employed, and the fact that the final convolution is at an angle to the axis of the setscrew, the resulting angled force on the leading thread can cause the setscrew to tilt within the bore of the connector block. Either of these situations can result in the setscrew becoming lodged in the connector block and the need to scrap the entire pulse generator device—a relatively expensive proposition.

It is accordingly principal object of the present invention to provide an improved connector block/setscrew design that obviates the foregoing problems.

SUMMARY OF THE INVENTION

The present invention provides a connector block and lead-locking setscrew for use in a header of an implantable pulse generator. The connector block has a longitudinal bore extending through its thickness dimension, which is adapted to receive a proximal terminal pin of a medical lead therethrough. Extending transversely to the longitudinal bore is a stepped bore that intersects the longitudinal bore. The stepped bore is internally threaded over only a predetermined portion thereof and the threads terminate in an undercut section having an annular, planar, 360-degree surface where that surface is perpendicular to a central axis of the transverse bore. The setscrew utilized has a proximal end and a distal end and has external threads on a predetermined portion that are designed to mate with the threads in the transverse bore of the connector block. The mentioned predetermined portion extends from the setscrew's proximal end toward, but short of, its distal end. The unthreaded distal end portion of the setscrew is of a lesser diameter than the predetermined portion that is threaded and thereby defines a 360-degree shoulder on the setscrew that is in a plane that is perpendicular to a longitudinal axis of the setscrew. Now, when the setscrew is screwed into the transverse bore of the connector block, the shoulder on the setscrew engages the annular, planar 360 degree surface provided in the connector block to prevent any possible damage to the threads on the setscrew or any angled forces that may cant the setscrew within the transverse bore in the connector block.

DESCRIPTION OF THE DRAWINGS

The foregoing features, objects and advantages of the invention will become apparent to those skilled in the art from the following detailed description of a preferred embodiment, especially when considered in conjunction with the accompanying drawings.

DESCRIPTION OF THE PREFERRED EMBODIMENT

Figure 1:
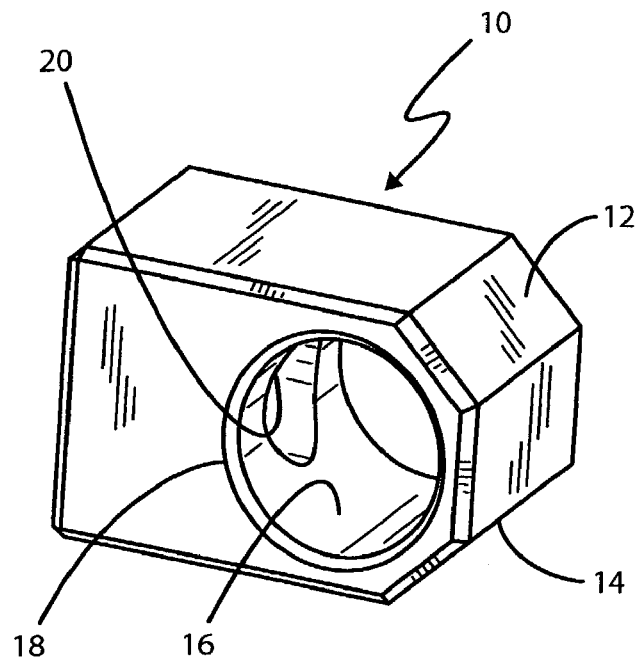
FIG. 1 is a perspective view of a prior art connector block.

Before describing the present invention, it is believed beneficial to first illustrate the typical prior art connector block/setscrew combination over which the present invention is deemed to be an improvement. Focusing attention first to FIG. 1, the connector block 10 is seen to comprise a block of a suitable metal, such as a titanium alloy or stainless steel alloy, having a generally rectangular configuration but with two 45-degree beveled edges 12 and 14. Formed through the thickness dimension of the connector block 10 is a first bore 16 having a beveled entrance at 18 to facilitate insertion of the proximal terminal pin of a medical lead through the bore 16. Extending transversely to the first bore 16 is a second bore 20 which is threaded along a length as represented by the dotted lines 22 in the cross-sectional view of FIG. 2. The overall length of the connector block 10 may be about 0.2 in. and its thickness may be about 0.15 in.

It can be seen that the bore 20 is not threaded over its entire length, but the thread stops short of the point where the bore 20 intersects with the bore 16. Specifically, the thread depth has been identified by line 24 in FIG. 2. The innermost thread or groove of the connector block 10 gradually reduces in size and terminates within 360-degrees around the circumferential. It is designed to mate with the external leading thread of the setscrew employed.

Figure 3:
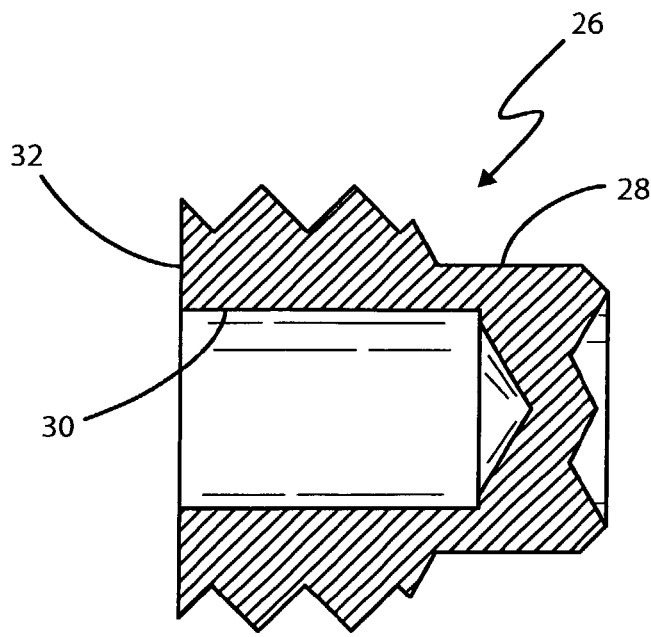
FIG. 3 is a cross-sectional view taken through a prior art setscrew.

In FIG. 3 a prior art setscrew is identified by numeral 26. The setscrew may have a standard 2-56 UNC-2A screw thread and may have an overall length of about 0.083 in. and is threaded over about 0.58 in. of its length. This lead is approximately 0.024 in. unthreaded at its distal end portion 28. A hex socket 30 is formed inward from a proximal end 32 for receiving a L-wrench or torqueing tool.

Figure 2:
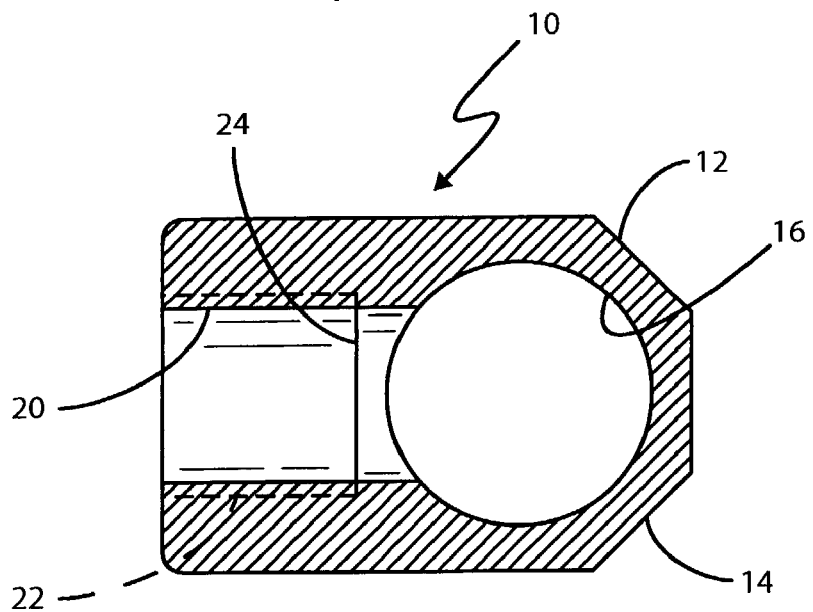
FIG. 2 is a longitudinal cross sectional view taken through the prior art connector block of FIG. 1.
Figure 4:
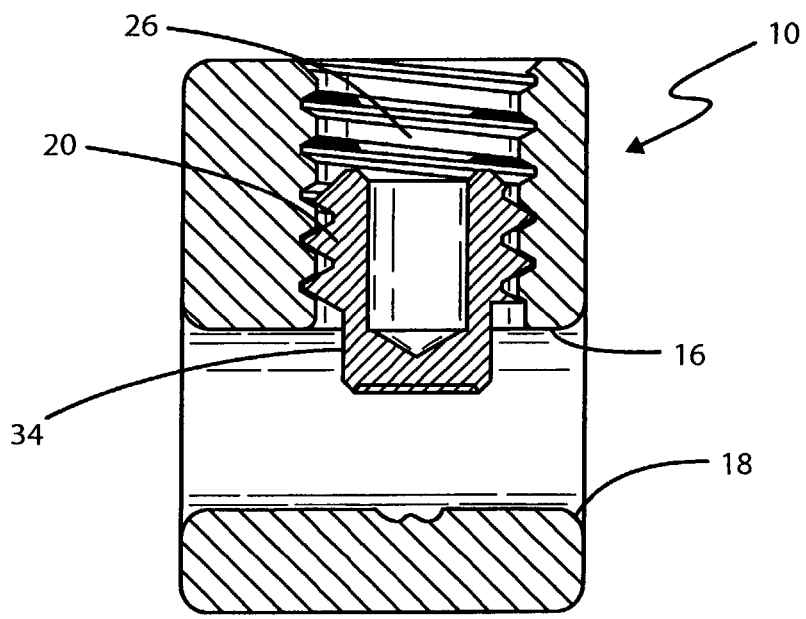
FIG. 4 is a greatly enlarged sectioned view of a prior art connector block and setscrew.

FIG. 4 is a greatly enlarged cross-sectional view taken through the connector block of FIG. 2 with the prior art setscrew of FIG. 3 inserted in the bore 20. Here, the leading thread of the setscrew extends past the existing threaded area of the connector block, causing the unmated portion of the leading setscrew thread to scrape against the non-threaded area of the connector block. This may happen, for example, if the setscrew is advanced before a proximal terminal pin of a medical lead has been fully inserted into the barrel of a header in which the prior art connector block and setscrew are used. When torque is applied in this situation, the sharp edge on the leading thread of the setscrew often breaks off, creating a burr and making it difficult, if not impossible, to retract the setscrew without damage to the connector block. Also, given the fact that the length of the setscrew will typically only be about 0.083 in. in length, the slanted wall of the helical thread results in a force on the leading thread that causes the setscrew to tilt or cant within the transversely extending bore. Such an event also results in a situation where the setscrew cannot be removed without damage to the pulse generator assembly and the need to scrap the device.

FIGS. 5–8 serve to illustrate the features of the present invention that obviate the foregoing problems attendant in the prior art design. It is designed to be inserted in a side entry slot of the header of an implantable electrical tissue stimulating device. Here, the connector block 100 is generally rectangular in form, but has beveled leading edges 112 and 114. A first bore 116, having a beveled leading edge 118, extends entirely through the thickness dimension of the block 100. Intersecting with the bore 116 is a transversely extending bore 120. More particularly, and with reference to FIG. 6, the bore 120 has a counterbore 121 that is threaded over its entire length as indicated by the dashed line 122. An undercut 125 is formed at the end of the threaded area so as to define a planar surface 126 that extends 360-degrees and is perpendicular to the central axis of the bore 120 and the counterbore 121. Without limitation, for receiving the terminal pin of an IS-1 lead, the connector block may be 0.222 in. long, 0.150 in. wide and 0.150 in. deep. The bore 116 maybe 0.111 inch in diameter, and the bore 120 may be 0.051 inch in diameter. The undercut may be 0.090 inch in diameter and 0.010 in depth. The bore 121 is drilled and tapped to receive a 2-56 UNC-2A setscrew.

Figure 5:
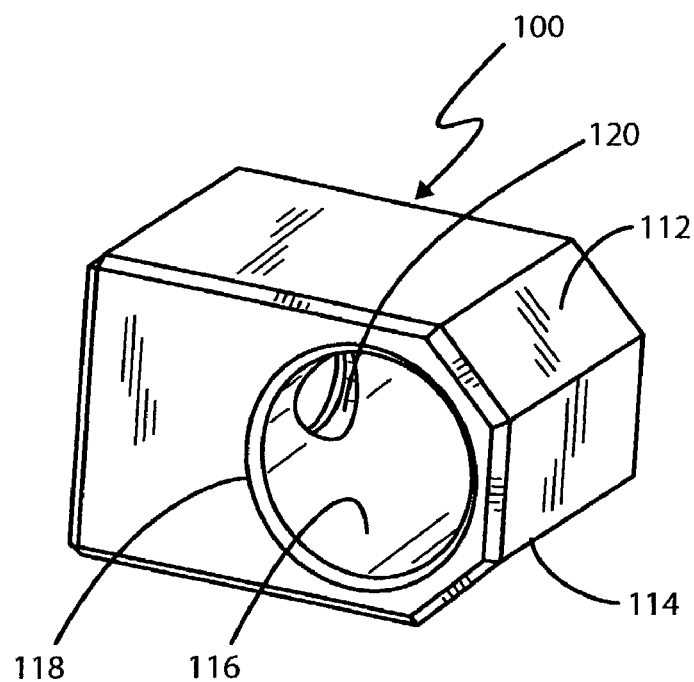
FIG. 5 is a perspective view of a connector block made in accordance with the present invention.
Figure 6:
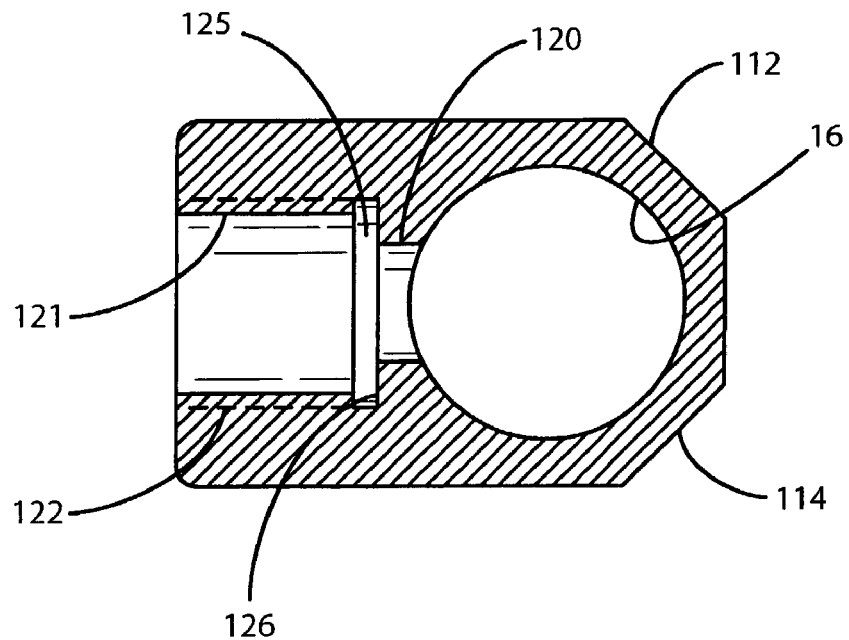
FIG. 6 is a longitudinal cross-sectional view taken through the connector block of FIG. 5.
Figure 7:
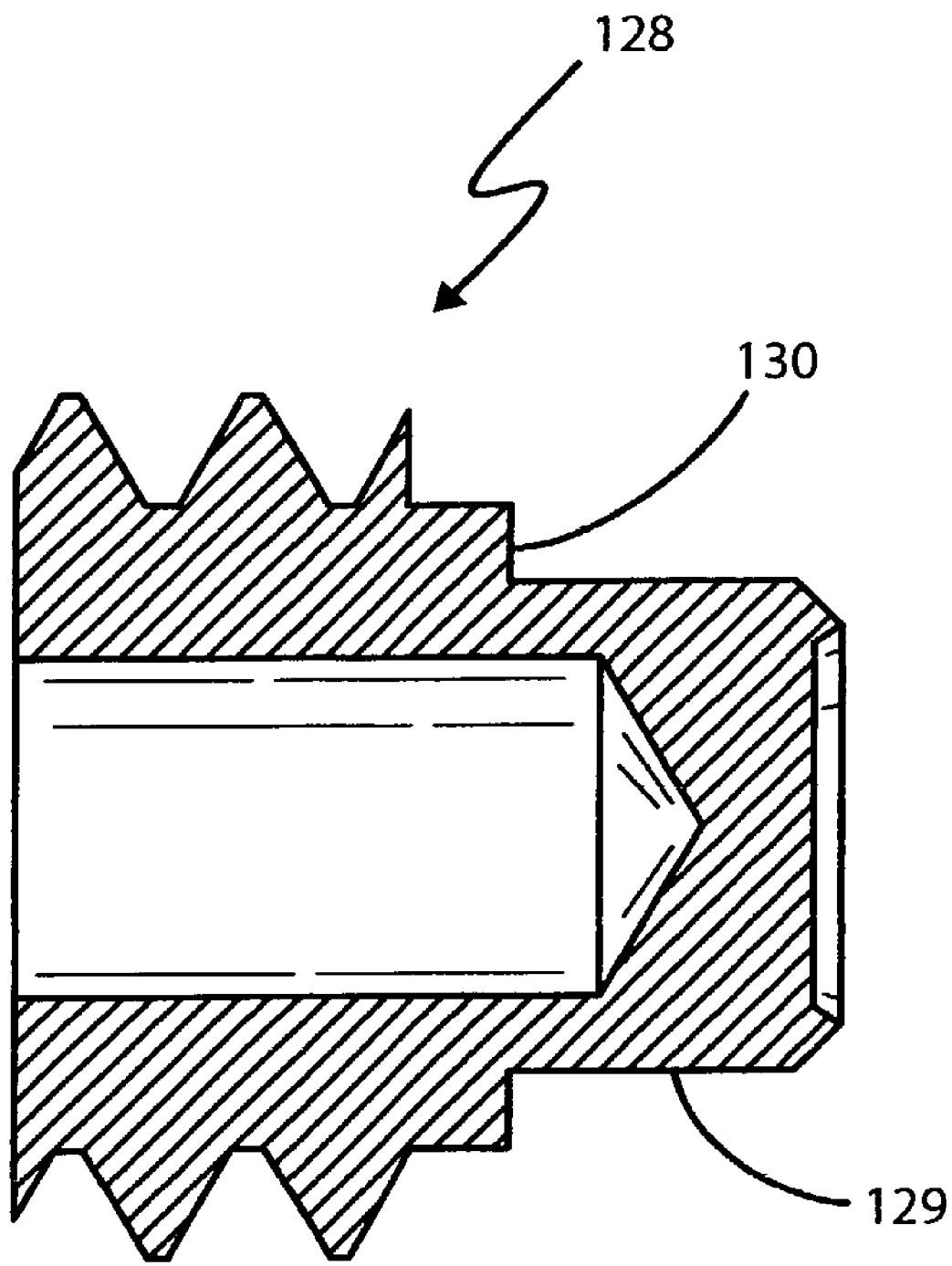
FIG. 7 is a cross-sectional view of a setscrew to be used with the connector block of FIGS. 5 and 6.

Turning next to FIG. 7, the setscrew used with the connector block of FIGS. 5 and 6 is identified generally by numeral 128 and differs from the prior art setscrew of FIG. 3 by the fact that it has non-threaded portions at its end that are machined to a smaller diameter, thus creating a 360-degree flat surface 130. The surface 130 is designed to mate with the surface 126 defined by the undercut on the connector block 100. This arrangement eliminates the thread interface of the setscrew and the connector block from acting as a mechanical stop as in the prior art design. In the present design, when the set screw is screwed all the way down, they do not contact each other if the lead pin is in place, but with no proximal lead terminal inserted through the connector block bore 116, the stepped area 130 of the setscrew 128 abuts the flat surface 126 to stop further advancement. As torque is applied to the setscrew, the flat area on the connector block presses against the mating flat area on the setscrew uniformly in the axial direction, inhibiting any tendency of the setscrew to tip or cant. Because of the manner in which the flat contact surfaces on the undercut 125 and the shoulder 130 interact, no burrs can occur. This eliminates the possibility of thread damage. Again, without limitation, for use with the connector block 100 described above, the setscrew 128 is a 2-56 UNC-2A setscrew that may be 0.831 inch in length and with a root diameter of 0.0648 inch. Its unthreaded portion 129 may be 0.033 inch long and 0.048 inch in diameter. This leaves the shoulder 130 about 0.0084 inch wide.

Figure 8:
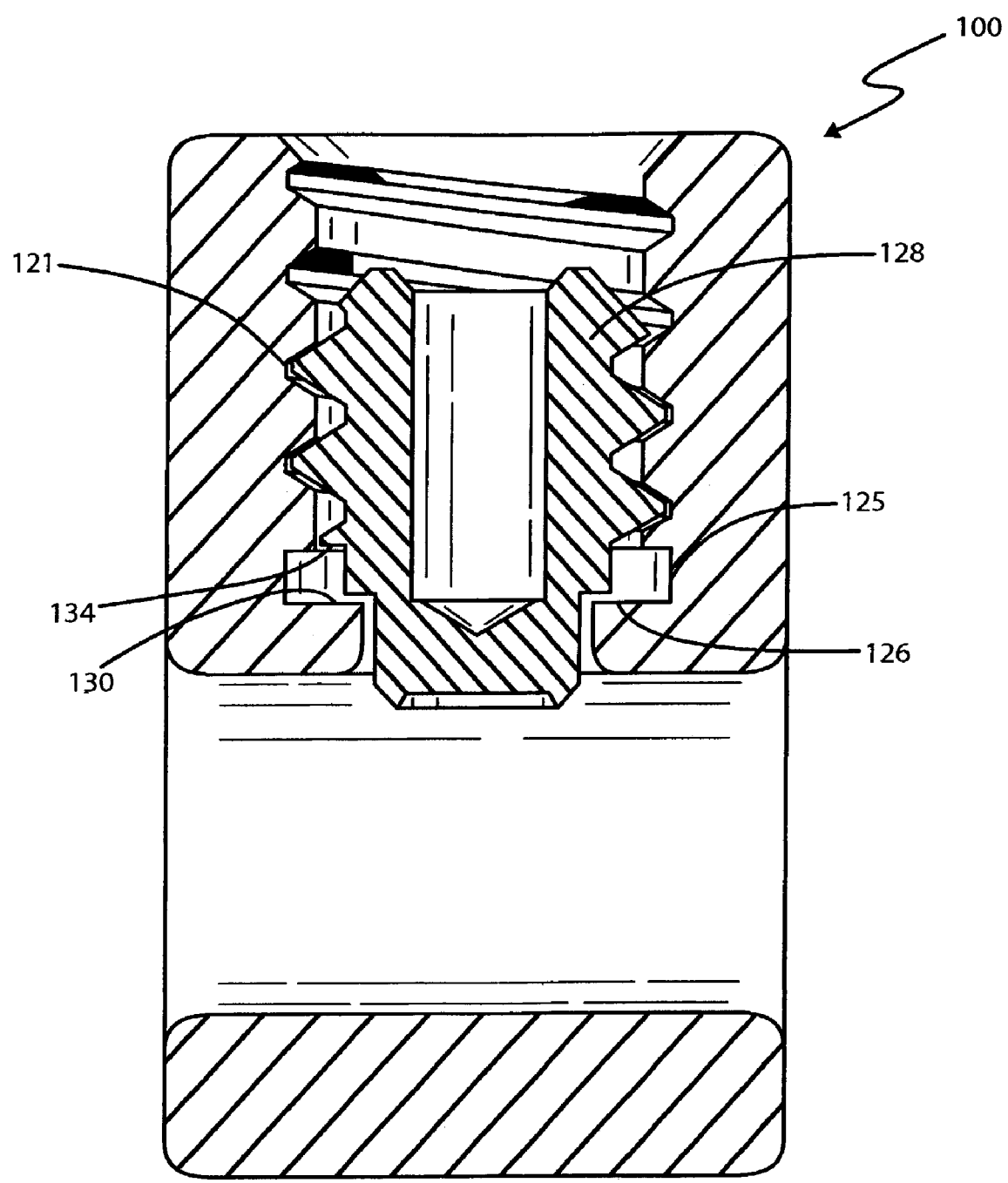
FIG. 8 is a greatly enlarged photomicrograph of a sectioned connector block of the present invention having a setscrew threaded therein.

FIG. 8 shows the connector block 100 and the setscrew 128 cut in half. The lowermost thread 134 ends at the undercut 125 and the flat annular surface 126 formed in the connector block abuts the shoulder 130 formed on the setscrew when the setscrew is advanced as far as it can go in the threaded bore 121.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

The invention claimed is:

1. In an implantable pulse generator of the type including a hermetically sealed housing containing an electrical circuit having input nodes and output nodes, a feed-through assembly having conductive pins connected to the input nodes and output nodes, a header having a longitudinal bore adapted to receive a proximal terminal of a medical lead and at least one electrical connector block disposed in said longitudinal bore and connected to a conductive pin of the feedthrough assembly, the connector block including a first bore through a thickness dimension thereof and generally coaxially aligned with the longitudinal bore, the connector block further including a transversely extending bore that intersects the first bore, the improvement comprising:

(a) internal threads in the transversely extending bore of the connector block extending from an exterior surface of the connector block to an annular-undercut that is disposed a predetermined distance inward of the first bore to form a 360-degree flat surface; and (b) a setscrew having a proximal end and distal end with external threads on a predetermined portion of the setscrew extending from the proximal end toward, but short of, the distal end and with an unthreaded distal end portion being of a lesser diameter than the predetermined portion that is threaded to define a 360-degree shoulder on the setscrew that is in a plane that is perpendicular to the longitudinal axis of the setscrew, where the 360-degree shoulder is adapted to butt against the 360-degree flat surface of the annular undercut in the connector block when the distal end of the setscrew has entered the first bore of the connector block.

2. The device of claim 1 wherein the annular undercut has a diameter of about 0.090 inch and a length of about 0.010 inch.

3. The device of claim 2 wherein the setscrew has its unthreaded distal portion of about 0.048 inch in diameter and 0.033 inch in length and the shoulder is about 0.0084 inch wide.

4. In combination, a connector block and a lead-locking setscrew for use in a header of an implantable pulse generator comprising:

(a) a connector block having a longitudinal bore adapted to receive a proximal terminal pin of a medical lead therethrough and a stepped transverse bore intersecting the longitudinal bore, the stepped transverse bore being threaded over only a predetermined portion thereof and terminating in a lesser diameter defining an undercut section having an annular planar 360-degree surface that is perpendicular to a central axis of the transverse bore; and (b) a setscrew having a proximal end and a distal end with external threads on a predetermined portion of the setscrew for mating with the threads in the transverse bore of the connector block in said predetermined portion extending from the proximal end toward, but short of, the distal end and with an unthreaded distal end portion being of a lesser diameter than the predetermined portion that is threaded to define an annular 360-degree shoulder on the setscrew that is in a plane that is perpendicular to a longitudinal axis of the setscrew whereby when the setscrew is screwed into the transverse bore of the connector block, the annular 360-degree shoulder on the setscrew engages the annular, planar, 360-degree surface of the connector block, preventing thread damage or canting of the setscrew.

5. The combination of claim 4 wherein the setscrew further includes a recess in the distal end thereof.

* * * * *